US007312070B2

United States Patent
Park et al.

(10) Patent No.: US 7,312,070 B2
(45) Date of Patent: Dec. 25, 2007

(54) β-CATENIN OLIGONUCLEOTIDE MICROCHIP AND METHOD FOR DETECTING β-CATENIN MUTATIONS EMPLOYING SAME

(75) Inventors: Jae-Gahb Park, Seoul (KR); Il-Jin Kim, Seoul (KR); Hio-Chung Kang, Seoul (KR); Jae-Hyun Park, Seoul (KR)

(73) Assignee: National Cancer Center (KR)

( * ) Notice: Subject to any disclaimer, the term of this patent is extended or adjusted under 35 U.S.C. 154(b) by 543 days.

(21) Appl. No.: 10/659,583

(22) Filed: Sep. 9, 2003

(65) Prior Publication Data

US 2005/0176016 A1    Aug. 11, 2005

(30) Foreign Application Priority Data

Jan. 8, 2003   (KR)   ............... 10-2003-0000987

(51) Int. Cl.
   *C12Q 1/68*   (2006.01)
   *C12M 1/38*   (2006.01)
   *C07H 21/04*  (2006.01)

(52) U.S. Cl. ............... 435/287.2; 435/6; 536/24.3

(58) Field of Classification Search ............... None
   See application file for complete search history.

(56) References Cited

U.S. PATENT DOCUMENTS 5,474,796 A * 12/1995 Brennan ............... 427/2.13

OTHER PUBLICATIONS

Kim et al. Clinical Cancer Research 2003 vol. 9 p. 2920-2925.*
El-Rifai International 2001 Jorunal of Cancer vol. 93 p. 832-838.*
Udatsu et al. Pediatr Surg Int 2001 vol. 17 p. 508.*
Abraham et al. American Journal of Pathology 2001 vol. 158 p. 1073.*
GenBank Accession No. Z019054 NCBI website Dec. 20, 1999.*
Hacia et al. Genome Research1998 vol. 8 p. 1245.*
Fujimori et al. 2001 Cancer Research vol. 61 p. 6656.*
National Library of Medicine, Bioessays, Dec. 21, 1999 (12): 1021-30, beta-catenin signaling and cancer, Morin PJ.
Il-Jin Kim, et al., RET Oligonucleotide Microarry for the Detection of RET Mutations in Multiple Endocrine Neoplasia Type 2 Syndromes, Clinical Cancer Research, vol. 8, 457-463, Feb. 2002.
Y. Yamada, B-Catenin mutation is selected during malignant transformation in colon carcinogenesis, Carcinogenesis, vol. 24, No. 1, pp. 91-97, 2003.
Wen-Hsiang Wen, et al., Comparison of TP53 Mutations Identified by Oligonucleotide Microarray and Conventional DNA Sequence Analysis, Cancer Research 60, 2716-2722, May 15, 2000.

* cited by examiner

*Primary Examiner*—Jeanine A. Goldberg
*Assistant Examiner*—Katherine Salmon
(74) *Attorney, Agent, or Firm*—Anderson Kill & Olick, PC

(57) ABSTRACT

The present invention relates to a β-catenin oligonucleotide microchip for detecting mutation in the mutational hot spot regions of β-catenin gene, a manufacturing process thereof and a method for detecting the β-catenin mutation employing same, wherein specific oligonucleotides are selectively designed to detect various missense mutations and in-frame deletion at the mutational hot spots of β-catenin gene. The β-catenin oligo chip of the present invention can be used in studies to detect β-catenin mutations and unravel the signal transduction mechanism and tumorigenesis related to β-catenin gene.

1 Claim, 2 Drawing Sheets

SEQUENCE LISTING

```
<160> NUMBER OF SEQ ID NOS: 127

<210> SEQ ID NO 1
<211> LENGTH: 21
<212> TYPE: DNA
<213> ORGANISM: Artificial Sequence
<220> FEATURE:
<223> OTHER INFORMATION: 29W

<400> SEQUENCE: 1
cagcaacagt cttacctgga c                                                 21

<210> SEQ ID NO 2
<211> LENGTH: 21
<212> TYPE: DNA
<213> ORGANISM: Artificial Sequence
<220> FEATURE:
<223> OTHER INFORMATION: 29M1

<400> SEQUENCE: 2
gcagcaacag acttacctgg a                                                 21

<210> SEQ ID NO 3
<211> LENGTH: 21
<212> TYPE: DNA
<213> ORGANISM: Artificial Sequence
<220> FEATURE:
<223> OTHER INFORMATION: 29M2

<400> SEQUENCE: 3
gcagcaacag gcttacctgg a                                                 21

<210> SEQ ID NO 4
<211> LENGTH: 21
<212> TYPE: DNA
<213> ORGANISM: Artificial Sequence
<220> FEATURE:
<223> OTHER INFORMATION: 29M3
```

```
<400> SEQUENCE: 4
gcagcaacag ccttacctgg a                                              21

<210> SEQ ID NO 5
<211> LENGTH: 21
<212> TYPE: DNA
<213> ORGANISM: Artificial Sequence
<220> FEATURE:
<223> OTHER INFORMATION: 29M4

<400> SEQUENCE: 5
cagcaacagt attacctgga c                                              21

<210> SEQ ID NO 6
<211> LENGTH: 21
<212> TYPE: DNA
<213> ORGANISM: Artificial Sequence
<220> FEATURE:
<223> OTHER INFORMATION: 29M5

<400> SEQUENCE: 6
cagcaacagt gttacctgga c                                              21

<210> SEQ ID NO 7
<211> LENGTH: 21
<212> TYPE: DNA
<213> ORGANISM: Artificial Sequence
<220> FEATURE:
<223> OTHER INFORMATION: 29M6

<400> SEQUENCE: 7
cagcaacagt tttacctgga c                                              21

<210> SEQ ID NO 8
<211> LENGTH: 21
<212> TYPE: DNA
<213> ORGANISM: Artificial Sequence
<220> FEATURE:
<223> OTHER INFORMATION: 29M7

<400> SEQUENCE: 8
agcaacagtc atacctggac t                                              21

<210> SEQ ID NO 9
<211> LENGTH: 21
<212> TYPE: DNA
<213> ORGANISM: Artificial Sequence
<220> FEATURE:
<223> OTHER INFORMATION: 29M8

<400> SEQUENCE: 9
agcaacagtc gtacctggac t                                              21

<210> SEQ ID NO 10
<211> LENGTH: 21
<212> TYPE: DNA
<213> ORGANISM: Artificial Sequence
<220> FEATURE:
<223> OTHER INFORMATION: 29M9

<400> SEQUENCE: 10
agcaacagtc ctacctggac t                                              21

<210> SEQ ID NO 11
```

-continued

```
<211> LENGTH: 21
<212> TYPE: DNA
<213> ORGANISM: Artificial Sequence
<220> FEATURE:
<223> OTHER INFORMATION: 29D

<400> SEQUENCE: 11
ggcagcaaca gtacctggac t                                              21

<210> SEQ ID NO 12
<211> LENGTH: 21
<212> TYPE: DNA
<213> ORGANISM: Artificial Sequence
<220> FEATURE:
<223> OTHER INFORMATION: 31W

<400> SEQUENCE: 12
cagtcttacc tggactctgg a                                              21

<210> SEQ ID NO 13
<211> LENGTH: 21
<212> TYPE: DNA
<213> ORGANISM: Artificial Sequence
<220> FEATURE:
<223> OTHER INFORMATION: 31M1

<400> SEQUENCE: 13
acagtcttac atggactctg g                                              21

<210> SEQ ID NO 14
<211> LENGTH: 21
<212> TYPE: DNA
<213> ORGANISM: Artificial Sequence
<220> FEATURE:
<223> OTHER INFORMATION: 31M2

<400> SEQUENCE: 14
acagtcttac ttggactctg g                                              21

<210> SEQ ID NO 15
<211> LENGTH: 21
<212> TYPE: DNA
<213> ORGANISM: Artificial Sequence
<220> FEATURE:
<223> OTHER INFORMATION: 31M3

<400> SEQUENCE: 15
acagtcttac gtggactctg g                                              21

<210> SEQ ID NO 16
<211> LENGTH: 21
<212> TYPE: DNA
<213> ORGANISM: Artificial Sequence
<220> FEATURE:
<223> OTHER INFORMATION: 31M4

<400> SEQUENCE: 16
cagtcttacc aggactctgg a                                              21

<210> SEQ ID NO 17
<211> LENGTH: 21
<212> TYPE: DNA
<213> ORGANISM: Artificial Sequence
<220> FEATURE:
<223> OTHER INFORMATION: 31M5

<400> SEQUENCE: 17
```
cagtcttacc gggactctgg a                                    21

<210> SEQ ID NO 18
<211> LENGTH: 21
<212> TYPE: DNA
<213> ORGANISM: Artificial Sequence
<220> FEATURE:
<223> OTHER INFORMATION: 31M6

<400> SEQUENCE: 18
cagtcttacc cggactctgg a                                    21

<210> SEQ ID NO 19
<211> LENGTH: 21
<212> TYPE: DNA
<213> ORGANISM: Artificial Sequence
<220> FEATURE:
<223> OTHER INFORMATION: 31M7

<400> SEQUENCE: 19
agtcttacct agactctgga a                                    21

<210> SEQ ID NO 20
<211> LENGTH: 21
<212> TYPE: DNA
<213> ORGANISM: Artificial Sequence
<220> FEATURE:
<223> OTHER INFORMATION: 31M8

<400> SEQUENCE: 20
agtcttacct cgactctgga a                                    21

<210> SEQ ID NO 21
<211> LENGTH: 21
<212> TYPE: DNA
<213> ORGANISM: Artificial Sequence
<220> FEATURE:
<223> OTHER INFORMATION: 31M9

<400> SEQUENCE: 21
agtcttacct tgactctgga a                                    21

<210> SEQ ID NO 22
<211> LENGTH: 21
<212> TYPE: DNA
<213> ORGANISM: Artificial Sequence
<220> FEATURE:
<223> OTHER INFORMATION: 31D

<400> SEQUENCE: 22
aacagtctta cgactctgga a                                    21

<210> SEQ ID NO 23
<211> LENGTH: 21
<212> TYPE: DNA
<213> ORGANISM: Artificial Sequence
<220> FEATURE:
<223> OTHER INFORMATION: 32W

<400> SEQUENCE: 23
tcttacctgg actctggaat c                                    21

<210> SEQ ID NO 24
<211> LENGTH: 21
<212> TYPE: DNA

```
<213> ORGANISM: Artificial Sequence
<220> FEATURE:
<223> OTHER INFORMATION: 32M1

<400> SEQUENCE: 24
gtcttacctg cactctggaa t                                              21

<210> SEQ ID NO 25
<211> LENGTH: 21
<212> TYPE: DNA
<213> ORGANISM: Artificial Sequence
<220> FEATURE:
<223> OTHER INFORMATION: 32M2

<400> SEQUENCE: 25
gtcttacctg tactctggaa t                                              21

<210> SEQ ID NO 26
<211> LENGTH: 21
<212> TYPE: DNA
<213> ORGANISM: Artificial Sequence
<220> FEATURE:
<223> OTHER INFORMATION: 32M3

<400> SEQUENCE: 26
gtcttacctg aactctggaa t                                              21

<210> SEQ ID NO 27
<211> LENGTH: 21
<212> TYPE: DNA
<213> ORGANISM: Artificial Sequence
<220> FEATURE:
<223> OTHER INFORMATION: 32M4

<400> SEQUENCE: 27
tcttacctgg cctctggaat c                                              21

<210> SEQ ID NO 28
<211> LENGTH: 21
<212> TYPE: DNA
<213> ORGANISM: Artificial Sequence
<220> FEATURE:
<223> OTHER INFORMATION: 32M5

<400> SEQUENCE: 28
tcttacctgg tctctggaat c                                              21

<210> SEQ ID NO 29
<211> LENGTH: 21
<212> TYPE: DNA
<213> ORGANISM: Artificial Sequence
<220> FEATURE:
<223> OTHER INFORMATION: 32M6

<400> SEQUENCE: 29
tcttacctgg gctctggaat c                                              21

<210> SEQ ID NO 30
<211> LENGTH: 21
<212> TYPE: DNA
<213> ORGANISM: Artificial Sequence
<220> FEATURE:
<223> OTHER INFORMATION: 32M7

<400> SEQUENCE: 30
cttacctgga gtctggaatc c                                              21
```

<210> SEQ ID NO 31
<211> LENGTH: 21
<212> TYPE: DNA
<213> ORGANISM: Artificial Sequence
<220> FEATURE:
<223> OTHER INFORMATION: 32M8

<400> SEQUENCE: 31
cttacctgga ttctggaatc c                                     21

<210> SEQ ID NO 32
<211> LENGTH: 21
<212> TYPE: DNA
<213> ORGANISM: Artificial Sequence
<220> FEATURE:
<223> OTHER INFORMATION: 32M9

<400> SEQUENCE: 32
cttacctgga atctggaatc c                                     21

<210> SEQ ID NO 33
<211> LENGTH: 21
<212> TYPE: DNA
<213> ORGANISM: Artificial Sequence
<220> FEATURE:
<223> OTHER INFORMATION: 32D

<400> SEQUENCE: 33
agtcttacct gtctggaatc c                                     21

<210> SEQ ID NO 34
<211> LENGTH: 21
<212> TYPE: DNA
<213> ORGANISM: Artificial Sequence
<220> FEATURE:
<223> OTHER INFORMATION: 33W

<400> SEQUENCE: 34
tacctggact ctggaatcca t                                     21

<210> SEQ ID NO 35
<211> LENGTH: 21
<212> TYPE: DNA
<213> ORGANISM: Artificial Sequence
<220> FEATURE:
<223> OTHER INFORMATION: 33M1

<400> SEQUENCE: 35
ttacctggac actggaatcc a                                     21

<210> SEQ ID NO 36
<211> LENGTH: 21
<212> TYPE: DNA
<213> ORGANISM: Artificial Sequence
<220> FEATURE:
<223> OTHER INFORMATION: 33M2

<400> SEQUENCE: 36
ttacctggac gctggaatcc a                                     21

<210> SEQ ID NO 37
<211> LENGTH: 21
<212> TYPE: DNA
<213> ORGANISM: Artificial Sequence
<220> FEATURE:

<223> OTHER INFORMATION: 33M3

<400> SEQUENCE: 37
ttacctggac cctggaatcc a                                              21

<210> SEQ ID NO 38
<211> LENGTH: 21
<212> TYPE: DNA
<213> ORGANISM: Artificial Sequence
<220> FEATURE:
<223> OTHER INFORMATION: 33M4

<400> SEQUENCE: 38
tacctggact gtggaatcca t                                              21

<210> SEQ ID NO 39
<211> LENGTH: 21
<212> TYPE: DNA
<213> ORGANISM: Artificial Sequence
<220> FEATURE:
<223> OTHER INFORMATION: 33M5

<400> SEQUENCE: 39
tacctggact atggaatcca t                                              21

<210> SEQ ID NO 40
<211> LENGTH: 21
<212> TYPE: DNA
<213> ORGANISM: Artificial Sequence
<220> FEATURE:
<223> OTHER INFORMATION: 33M6

<400> SEQUENCE: 40
tacctggact ttggaatcca t                                              21

<210> SEQ ID NO 41
<211> LENGTH: 21
<212> TYPE: DNA
<213> ORGANISM: Artificial Sequence
<220> FEATURE:
<223> OTHER INFORMATION: 33M7

<400> SEQUENCE: 41
acctggactc aggaatccat t                                              21

<210> SEQ ID NO 42
<211> LENGTH: 21
<212> TYPE: DNA
<213> ORGANISM: Artificial Sequence
<220> FEATURE:
<223> OTHER INFORMATION: 33M8

<400> SEQUENCE: 42
acctggactc gggaatccat t                                              21

<210> SEQ ID NO 43
<211> LENGTH: 21
<212> TYPE: DNA
<213> ORGANISM: Artificial Sequence
<220> FEATURE:
<223> OTHER INFORMATION: 33M9

<400> SEQUENCE: 43
acctggactc cggaatccat t                                              21

```
<210> SEQ ID NO 44
<211> LENGTH: 21
<212> TYPE: DNA
<213> ORGANISM: Artificial Sequence
<220> FEATURE:
<223> OTHER INFORMATION: 33D

<400> SEQUENCE: 44
ttacctggac ggaatccatt c                                              21

<210> SEQ ID NO 45
<211> LENGTH: 21
<212> TYPE: DNA
<213> ORGANISM: Artificial Sequence
<220> FEATURE:
<223> OTHER INFORMATION: 34W

<400> SEQUENCE: 45
ctggactctg gaatccattc t                                              21

<210> SEQ ID NO 46
<211> LENGTH: 21
<212> TYPE: DNA
<213> ORGANISM: Artificial Sequence
<220> FEATURE:
<223> OTHER INFORMATION: 34M1

<400> SEQUENCE: 46
cctggactct tgaatccatt c                                              21

<210> SEQ ID NO 47
<211> LENGTH: 21
<212> TYPE: DNA
<213> ORGANISM: Artificial Sequence
<220> FEATURE:
<223> OTHER INFORMATION: 34M2

<400> SEQUENCE: 47
cctggactct agaatccatt c                                              21

<210> SEQ ID NO 48
<211> LENGTH: 21
<212> TYPE: DNA
<213> ORGANISM: Artificial Sequence
<220> FEATURE:
<223> OTHER INFORMATION: 34M3

<400> SEQUENCE: 48
cctggactct cgaatccatt c                                              21

<210> SEQ ID NO 49
<211> LENGTH: 21
<212> TYPE: DNA
<213> ORGANISM: Artificial Sequence
<220> FEATURE:
<223> OTHER INFORMATION: 34M4

<400> SEQUENCE: 49
ctggactctg taatccattc t                                              21

<210> SEQ ID NO 50
<211> LENGTH: 21
<212> TYPE: DNA
<213> ORGANISM: Artificial Sequence
<220> FEATURE:
<223> OTHER INFORMATION: 34M5
```

-continued

```
<400> SEQUENCE: 50
ctggactctg caatccattc t                                              21

<210> SEQ ID NO 51
<211> LENGTH: 21
<212> TYPE: DNA
<213> ORGANISM: Artificial Sequence
<220> FEATURE:
<223> OTHER INFORMATION: 34M6

<400> SEQUENCE: 51
ctggactctg aaatccattc t                                              21

<210> SEQ ID NO 52
<211> LENGTH: 21
<212> TYPE: DNA
<213> ORGANISM: Artificial Sequence
<220> FEATURE:
<223> OTHER INFORMATION: 34M7

<400> SEQUENCE: 52
tggactctgg tatccattct g                                              21

<210> SEQ ID NO 53
<211> LENGTH: 21
<212> TYPE: DNA
<213> ORGANISM: Artificial Sequence
<220> FEATURE:
<223> OTHER INFORMATION: 34M8

<400> SEQUENCE: 53
tggactctgg gatccattct g                                              21

<210> SEQ ID NO 54
<211> LENGTH: 21
<212> TYPE: DNA
<213> ORGANISM: Artificial Sequence
<220> FEATURE:
<223> OTHER INFORMATION: 34M9

<400> SEQUENCE: 54
tggactctgg catccattct g                                              21

<210> SEQ ID NO 55
<211> LENGTH: 21
<212> TYPE: DNA
<213> ORGANISM: Artificial Sequence
<220> FEATURE:
<223> OTHER INFORMATION: 34D

<400> SEQUENCE: 55
cctggactct atccattctg g                                              21

<210> SEQ ID NO 56
<211> LENGTH: 21
<212> TYPE: DNA
<213> ORGANISM: Artificial Sequence
<220> FEATURE:
<223> OTHER INFORMATION: 35W

<400> SEQUENCE: 56
gactctggaa tccattctgg t                                              21

<210> SEQ ID NO 57
<211> LENGTH: 21
```

<212> TYPE: DNA
<213> ORGANISM: Artificial Sequence
<220> FEATURE:
<223> OTHER INFORMATION: 35M1

<400> SEQUENCE: 57
ggactctgga gtccattctg g                                              21

<210> SEQ ID NO 58
<211> LENGTH: 21
<212> TYPE: DNA
<213> ORGANISM: Artificial Sequence
<220> FEATURE:
<223> OTHER INFORMATION: 35M2

<400> SEQUENCE: 58
ggactctgga ctccattctg g                                              21

<210> SEQ ID NO 59
<211> LENGTH: 21
<212> TYPE: DNA
<213> ORGANISM: Artificial Sequence
<220> FEATURE:
<223> OTHER INFORMATION: 35M3

<400> SEQUENCE: 59
ggactctgga ttccattctg g                                              21

<210> SEQ ID NO 60
<211> LENGTH: 21
<212> TYPE: DNA
<213> ORGANISM: Artificial Sequence
<220> FEATURE:
<223> OTHER INFORMATION: 35M4

<400> SEQUENCE: 60
gactctggaa cccattctgg t                                              21

<210> SEQ ID NO 61
<211> LENGTH: 21
<212> TYPE: DNA
<213> ORGANISM: Artificial Sequence
<220> FEATURE:
<223> OTHER INFORMATION: 35M5

<400> SEQUENCE: 61
gactctggaa gccattctgg t                                              21

<210> SEQ ID NO 62
<211> LENGTH: 21
<212> TYPE: DNA
<213> ORGANISM: Artificial Sequence
<220> FEATURE:
<223> OTHER INFORMATION: 35M6

<400> SEQUENCE: 62
gactctggaa accattctgg t                                              21

<210> SEQ ID NO 63
<211> LENGTH: 21
<212> TYPE: DNA
<213> ORGANISM: Artificial Sequence
<220> FEATURE:
<223> OTHER INFORMATION: 35M7

<400> SEQUENCE: 63
actctggaat gcattctggt g					21

<210> SEQ ID NO 64
<211> LENGTH: 21
<212> TYPE: DNA
<213> ORGANISM: Artificial Sequence
<220> FEATURE:
<223> OTHER INFORMATION: 35M8

<400> SEQUENCE: 64
actctggaat acattctggt g					21

<210> SEQ ID NO 65
<211> LENGTH: 21
<212> TYPE: DNA
<213> ORGANISM: Artificial Sequence
<220> FEATURE:
<223> OTHER INFORMATION: 35M9

<400> SEQUENCE: 65
actctggaat tcattctggt g					21

<210> SEQ ID NO 66
<211> LENGTH: 21
<212> TYPE: DNA
<213> ORGANISM: Artificial Sequence
<220> FEATURE:
<223> OTHER INFORMATION: 35D

<400> SEQUENCE: 66
ggactctgga cattctggtg c					21

<210> SEQ ID NO 67
<211> LENGTH: 21
<212> TYPE: DNA
<213> ORGANISM: Artificial Sequence
<220> FEATURE:
<223> OTHER INFORMATION: 37W

<400> SEQUENCE: 67
ggaatccatt ctggtgccac t					21

<210> SEQ ID NO 68
<211> LENGTH: 21
<212> TYPE: DNA
<213> ORGANISM: Artificial Sequence
<220> FEATURE:
<223> OTHER INFORMATION: 37M1

<400> SEQUENCE: 68
tggaatccat actggtgcca c					21

<210> SEQ ID NO 69
<211> LENGTH: 21
<212> TYPE: DNA
<213> ORGANISM: Artificial Sequence
<220> FEATURE:
<223> OTHER INFORMATION: 37M2

<400> SEQUENCE: 69
tggaatccat cctggtgcca c					21

<210> SEQ ID NO 70
<211> LENGTH: 21
<212> TYPE: DNA
<213> ORGANISM: Artificial Sequence

```
<220> FEATURE:
<223> OTHER INFORMATION: 37M3

<400> SEQUENCE: 70
tggaatccat gctggtgcca c                                              21

<210> SEQ ID NO 71
<211> LENGTH: 21
<212> TYPE: DNA
<213> ORGANISM: Artificial Sequence
<220> FEATURE:
<223> OTHER INFORMATION: 37M4

<400> SEQUENCE: 71
ggaatccatt atggtgccac t                                              21

<210> SEQ ID NO 72
<211> LENGTH: 21
<212> TYPE: DNA
<213> ORGANISM: Artificial Sequence
<220> FEATURE:
<223> OTHER INFORMATION: 37M5

<400> SEQUENCE: 72
ggaatccatt gtggtgccac t                                              21

<210> SEQ ID NO 73
<211> LENGTH: 21
<212> TYPE: DNA
<213> ORGANISM: Artificial Sequence
<220> FEATURE:
<223> OTHER INFORMATION: 37M6

<400> SEQUENCE: 73
ggaatccatt ttggtgccac t                                              21

<210> SEQ ID NO 74
<211> LENGTH: 21
<212> TYPE: DNA
<213> ORGANISM: Artificial Sequence
<220> FEATURE:
<223> OTHER INFORMATION: 37M7

<400> SEQUENCE: 74
gaatccattc aggtgccact a                                              21

<210> SEQ ID NO 75
<211> LENGTH: 21
<212> TYPE: DNA
<213> ORGANISM: Artificial Sequence
<220> FEATURE:
<223> OTHER INFORMATION: 37M8

<400> SEQUENCE: 75
gaatccattc gggtgccact a                                              21

<210> SEQ ID NO 76
<211> LENGTH: 21
<212> TYPE: DNA
<213> ORGANISM: Artificial Sequence
<220> FEATURE:
<223> OTHER INFORMATION: 37M9

<400> SEQUENCE: 76
gaatccattc cggtgccact a                                              21
```

<210> SEQ ID NO 77
<211> LENGTH: 21
<212> TYPE: DNA
<213> ORGANISM: Artificial Sequence
<220> FEATURE:
<223> OTHER INFORMATION: 37D

<400> SEQUENCE: 77
tggaatccat ggtgccacta c                                              21

<210> SEQ ID NO 78
<211> LENGTH: 21
<212> TYPE: DNA
<213> ORGANISM: Artificial Sequence
<220> FEATURE:
<223> OTHER INFORMATION: 38W

<400> SEQUENCE: 78
atccattctg gtgccactac c                                              21

<210> SEQ ID NO 79
<211> LENGTH: 21
<212> TYPE: DNA
<213> ORGANISM: Artificial Sequence
<220> FEATURE:
<223> OTHER INFORMATION: 38M1

<400> SEQUENCE: 79
aatccattct agtgccacta c                                              21

<210> SEQ ID NO 80
<211> LENGTH: 21
<212> TYPE: DNA
<213> ORGANISM: Artificial Sequence
<220> FEATURE:
<223> OTHER INFORMATION: 38M2

<400> SEQUENCE: 80
aatccattct cgtgccacta c                                              21

<210> SEQ ID NO 81
<211> LENGTH: 21
<212> TYPE: DNA
<213> ORGANISM: Artificial Sequence
<220> FEATURE:
<223> OTHER INFORMATION: 38M3

<400> SEQUENCE: 81
aatccattct tgtgccacta c                                              21

<210> SEQ ID NO 82
<211> LENGTH: 21
<212> TYPE: DNA
<213> ORGANISM: Artificial Sequence
<220> FEATURE:
<223> OTHER INFORMATION: 38M4

<400> SEQUENCE: 82
atccattctg atgccactac c                                              21

<210> SEQ ID NO 83
<211> LENGTH: 21
<212> TYPE: DNA
<213> ORGANISM: Artificial Sequence
<220> FEATURE:
<223> OTHER INFORMATION: 38M5

<400> SEQUENCE: 83
atccattctg ctgccactac c                                              21

<210> SEQ ID NO 84
<211> LENGTH: 21
<212> TYPE: DNA
<213> ORGANISM: Artificial Sequence
<220> FEATURE:
<223> OTHER INFORMATION: 38M6

<400> SEQUENCE: 84
atccattctg ttgccactac c                                              21

<210> SEQ ID NO 85
<211> LENGTH: 21
<212> TYPE: DNA
<213> ORGANISM: Artificial Sequence
<220> FEATURE:
<223> OTHER INFORMATION: 38M7

<400> SEQUENCE: 85
tccattctgg agccactacc a                                              21

<210> SEQ ID NO 86
<211> LENGTH: 21
<212> TYPE: DNA
<213> ORGANISM: Artificial Sequence
<220> FEATURE:
<223> OTHER INFORMATION: 38M8

<400> SEQUENCE: 86
tccattctgg ggccactacc a                                              21

<210> SEQ ID NO 87
<211> LENGTH: 21
<212> TYPE: DNA
<213> ORGANISM: Artificial Sequence
<220> FEATURE:
<223> OTHER INFORMATION: 38M9

<400> SEQUENCE: 87
tccattctgg cgccactacc a                                              21

<210> SEQ ID NO 88
<211> LENGTH: 21
<212> TYPE: DNA
<213> ORGANISM: Artificial Sequence
<220> FEATURE:
<223> OTHER INFORMATION: 38D

<400> SEQUENCE: 88
aatccattct gccactacca c                                              21

<210> SEQ ID NO 89
<211> LENGTH: 21
<212> TYPE: DNA
<213> ORGANISM: Artificial Sequence
<220> FEATURE:
<223> OTHER INFORMATION: 41W

<400> SEQUENCE: 89
ggtgccacta ccacagctcc t                                              21

<210> SEQ ID NO 90

-continued

```
<211> LENGTH: 21
<212> TYPE: DNA
<213> ORGANISM: Artificial Sequence
<220> FEATURE:
<223> OTHER INFORMATION: 41M1

<400> SEQUENCE: 90
tggtgccact tccacagctc c                                              21

<210> SEQ ID NO 91
<211> LENGTH: 21
<212> TYPE: DNA
<213> ORGANISM: Artificial Sequence
<220> FEATURE:
<223> OTHER INFORMATION: 41M2

<400> SEQUENCE: 91
tggtgccact gccacagctc c                                              21

<210> SEQ ID NO 92
<211> LENGTH: 21
<212> TYPE: DNA
<213> ORGANISM: Artificial Sequence
<220> FEATURE:
<223> OTHER INFORMATION: 41M3

<400> SEQUENCE: 92
tggtgccact cccacagctc c                                              21

<210> SEQ ID NO 93
<211> LENGTH: 21
<212> TYPE: DNA
<213> ORGANISM: Artificial Sequence
<220> FEATURE:
<223> OTHER INFORMATION: 41M4

<400> SEQUENCE: 93
ggtgccacta gcacagctcc t                                              21

<210> SEQ ID NO 94
<211> LENGTH: 21
<212> TYPE: DNA
<213> ORGANISM: Artificial Sequence
<220> FEATURE:
<223> OTHER INFORMATION: 41M5

<400> SEQUENCE: 94
ggtgccacta tcacagctcc t                                              21

<210> SEQ ID NO 95
<211> LENGTH: 21
<212> TYPE: DNA
<213> ORGANISM: Artificial Sequence
<220> FEATURE:
<223> OTHER INFORMATION: 41M6

<400> SEQUENCE: 95
ggtgccacta acacagctcc t                                              21

<210> SEQ ID NO 96
<211> LENGTH: 21
<212> TYPE: DNA
<213> ORGANISM: Artificial Sequence
<220> FEATURE:
<223> OTHER INFORMATION: 41M7

<400> SEQUENCE: 96
```
gtgccactac aacagctcct t    21

<210> SEQ ID NO 97
<211> LENGTH: 21
<212> TYPE: DNA
<213> ORGANISM: Artificial Sequence
<220> FEATURE:
<223> OTHER INFORMATION: 41M8

<400> SEQUENCE: 97
gtgccactac tacagctcct t    21

<210> SEQ ID NO 98
<211> LENGTH: 21
<212> TYPE: DNA
<213> ORGANISM: Artificial Sequence
<220> FEATURE:
<223> OTHER INFORMATION: 41M9

<400> SEQUENCE: 98
gtgccactac gacagctcct t    21

<210> SEQ ID NO 99
<211> LENGTH: 21
<212> TYPE: DNA
<213> ORGANISM: Artificial Sequence
<220> FEATURE:
<223> OTHER INFORMATION: 41D

<400> SEQUENCE: 99
tggtgccact acagctcctt c    21

<210> SEQ ID NO 100
<211> LENGTH: 21
<212> TYPE: DNA
<213> ORGANISM: Artificial Sequence
<220> FEATURE:
<223> OTHER INFORMATION: 45W

<400> SEQUENCE: 100
acagctcctt ctctgagtgg t    21

<210> SEQ ID NO 101
<211> LENGTH: 21
<212> TYPE: DNA
<213> ORGANISM: Artificial Sequence
<220> FEATURE:
<223> OTHER INFORMATION: 45M1

<400> SEQUENCE: 101
cacagctcct actctgagtg g    21

<210> SEQ ID NO 102
<211> LENGTH: 21
<212> TYPE: DNA
<213> ORGANISM: Artificial Sequence
<220> FEATURE:
<223> OTHER INFORMATION: 45M2

<400> SEQUENCE: 102
cacagctcct gctctgagtg g    21

<210> SEQ ID NO 103
<211> LENGTH: 21
<212> TYPE: DNA

```
<213> ORGANISM: Artificial Sequence
<220> FEATURE:
<223> OTHER INFORMATION: 45M3

<400> SEQUENCE: 103
cacagctcct cctctgagtg g                                              21

<210> SEQ ID NO 104
<211> LENGTH: 21
<212> TYPE: DNA
<213> ORGANISM: Artificial Sequence
<220> FEATURE:
<223> OTHER INFORMATION: 45M4

<400> SEQUENCE: 104
acagctcctt gtctgagtgg t                                              21

<210> SEQ ID NO 105
<211> LENGTH: 21
<212> TYPE: DNA
<213> ORGANISM: Artificial Sequence
<220> FEATURE:
<223> OTHER INFORMATION: 45M5

<400> SEQUENCE: 105
acagctcctt atctgagtgg t                                              21

<210> SEQ ID NO 106
<211> LENGTH: 21
<212> TYPE: DNA
<213> ORGANISM: Artificial Sequence
<220> FEATURE:
<223> OTHER INFORMATION: 45M6

<400> SEQUENCE: 106
acagctcctt ttctgagtgg t                                              21

<210> SEQ ID NO 107
<211> LENGTH: 21
<212> TYPE: DNA
<213> ORGANISM: Artificial Sequence
<220> FEATURE:
<223> OTHER INFORMATION: 45M7

<400> SEQUENCE: 107
cagctccttc actgagtggt a                                              21

<210> SEQ ID NO 108
<211> LENGTH: 21
<212> TYPE: DNA
<213> ORGANISM: Artificial Sequence
<220> FEATURE:
<223> OTHER INFORMATION: 45M8

<400> SEQUENCE: 108
cagctccttc gctgagtggt a                                              21

<210> SEQ ID NO 109
<211> LENGTH: 21
<212> TYPE: DNA
<213> ORGANISM: Artificial Sequence
<220> FEATURE:
<223> OTHER INFORMATION: 45M9

<400> SEQUENCE: 109
cagctccttc cctgagtggt a                                              21
```

<210> SEQ ID NO 110
<211> LENGTH: 21
<212> TYPE: DNA
<213> ORGANISM: Artificial Sequence
<220> FEATURE:
<223> OTHER INFORMATION: 45D

<400> SEQUENCE: 110
ccacagctcc tctgagtggt a                                              21

<210> SEQ ID NO 111
<211> LENGTH: 21
<212> TYPE: DNA
<213> ORGANISM: Artificial Sequence
<220> FEATURE:
<223> OTHER INFORMATION: 48W

<400> SEQUENCE: 111
tctctgagtg gtaaaggcaa t                                              21

<210> SEQ ID NO 112
<211> LENGTH: 21
<212> TYPE: DNA
<213> ORGANISM: Artificial Sequence
<220> FEATURE:
<223> OTHER INFORMATION: 48M1

<400> SEQUENCE: 112
ttctctgagt agtaaaggca a                                              21

<210> SEQ ID NO 113
<211> LENGTH: 21
<212> TYPE: DNA
<213> ORGANISM: Artificial Sequence
<220> FEATURE:
<223> OTHER INFORMATION: 48M2

<400> SEQUENCE: 113
ttctctgagt tgtaaaggca a                                              21

<210> SEQ ID NO 114
<211> LENGTH: 21
<212> TYPE: DNA
<213> ORGANISM: Artificial Sequence
<220> FEATURE:
<223> OTHER INFORMATION: 48M3

<400> SEQUENCE: 114
ttctctgagt cgtaaaggca a                                              21

<210> SEQ ID NO 115
<211> LENGTH: 21
<212> TYPE: DNA
<213> ORGANISM: Artificial Sequence
<220> FEATURE:
<223> OTHER INFORMATION: 48M4

<400> SEQUENCE: 115
tctctgagtg ataaaggcaa t                                              21

<210> SEQ ID NO 116
<211> LENGTH: 21
<212> TYPE: DNA
<213> ORGANISM: Artificial Sequence
<220> FEATURE:

```
<223> OTHER INFORMATION: 48M5

<400> SEQUENCE: 116
tctctgagtg ctaaaggcaa t                                              21

<210> SEQ ID NO 117
<211> LENGTH: 21
<212> TYPE: DNA
<213> ORGANISM: Artificial Sequence
<220> FEATURE:
<223> OTHER INFORMATION: 48M6

<400> SEQUENCE: 117
tctctgagtg ttaaaggcaa t                                              21

<210> SEQ ID NO 118
<211> LENGTH: 21
<212> TYPE: DNA
<213> ORGANISM: Artificial Sequence
<220> FEATURE:
<223> OTHER INFORMATION: 48M7

<400> SEQUENCE: 118
ctctgagtgg aaaaggcaat c                                              21

<210> SEQ ID NO 119
<211> LENGTH: 21
<212> TYPE: DNA
<213> ORGANISM: Artificial Sequence
<220> FEATURE:
<223> OTHER INFORMATION: 48M8

<400> SEQUENCE: 119
ctctgagtgg caaaggcaat c                                              21

<210> SEQ ID NO 120
<211> LENGTH: 21
<212> TYPE: DNA
<213> ORGANISM: Artificial Sequence
<220> FEATURE:
<223> OTHER INFORMATION: 48M9

<400> SEQUENCE: 120
ctctgagtgg gaaaggcaat c                                              21

<210> SEQ ID NO 121
<211> LENGTH: 21
<212> TYPE: DNA
<213> ORGANISM: Artificial Sequence
<220> FEATURE:
<223> OTHER INFORMATION: 48D

<400> SEQUENCE: 121
ttctctgagt aaaggcaatc c                                              21

<210> SEQ ID NO 122
<211> LENGTH: 22
<212> TYPE: DNA
<213> ORGANISM: Artificial Sequence
<220> FEATURE:
<223> OTHER INFORMATION: Exon-3F

<400> SEQUENCE: 122
gatttgatgg agttggacat gg                                             22
```

```
<210> SEQ ID NO 123
<211> LENGTH: 22
<212> TYPE: DNA
<213> ORGANISM: Artificial Sequence
<220> FEATURE:
<223> OTHER INFORMATION: Exon-3R

<400> SEQUENCE: 123
tgttcttgag tgaaggactg ag                                               22

<210> SEQ ID NO 124
<211> LENGTH: 21
<212> TYPE: DNA
<213> ORGANISM: Artificial Sequence
<220> FEATURE:
<223> OTHER INFORMATION: Long-3F

<400> SEQUENCE: 124
aaaatccagc gtggacaatg g                                                21

<210> SEQ ID NO 125
<211> LENGTH: 21
<212> TYPE: DNA
<213> ORGANISM: Artificial Sequence
<220> FEATURE:
<223> OTHER INFORMATION: Long-3R

<400> SEQUENCE: 125
tgtggcaagt tctgcatcat c                                                21

<210> SEQ ID NO 126
<211> LENGTH: 21
<212> TYPE: DNA
<213> ORGANISM: Artificial Sequence
<220> FEATURE:
<223> OTHER INFORMATION: BAT26-F

<400> SEQUENCE: 126
tgactacttt tgacttcagc c                                                21

<210> SEQ ID NO 127
<211> LENGTH: 22
<212> TYPE: DNA
<213> ORGANISM: Artificial Sequence
<220> FEATURE:
<223> OTHER INFORMATION: BAT26-R

<400> SEQUENCE: 127
aaccattcaa catttttaac cc                                               22
```

β-CATENIN OLIGONUCLEOTIDE MICROCHIP AND METHOD FOR DETECTING β-CATENIN MUTATIONS EMPLOYING SAME

FIELD OF THE INVENTION

The present invention relates to a β-catenin oligonucleotide microchip for detecting mutations in the mutational hot spot regions of β-catenin gene, a manufacturing process thereof and a method for detecting β-catenin mutations employing same.

BACKGROUND OF THE INVENTION

β-Catenin, which functions as a downstream transcriptional activator in the Wnt signaling pathway, is a submembrane component of the cadherin-mediated cell-cell adhesion system (Abraham, S. C. et al., *Am. J. Pathol.* 158:1005-1010, 2001; Abraham, S. C. et al., *Am. J. Pathol.* 158:1073-1078, 2001). *APC* (*adenomatus polyposis coli*) tumor suppressor protein, along with GSK-3β (glycogen synthase kinase-3β), promotes the phosphorylation of the serine/threeonine residues in exon 3 of the β-catenin gene (Abraham, S. C. et al., *Am. J. Pathol.* 158:1073-1078, 2001). Mutation of the *APC* gene or the β-catenin gene was found to result in the accumulation of β-catenin protein and the loss of β-catenin regulatory activity (Abraham, S. C. et al., *Am. J Pathol.* 158:1073-1078, 2001). The majority of β-catenin mutations have been reported at specific GSK-3β phosphorylation sites, i.e., Ser-33, Ser-37, Thr-41, Ser-45, and other residues (Asp-32 and Gly-34) in many human cancers, including endometrial, gastric, ovarian, hepatoblastomas, and colorectal cancers (Saegusa, M. and Okayasu, I. *J Pathol.* 194:59-67, 2001). In colorectal cancers, various frequencies of the β-catenin mutations have been reported, ranging from 0 to 16% (Nilbert, M. and Rambech, E. *Cancer Genet. Cytogenet.* 128:43-45, 2001; Mirabelli-Primdahl, L. et al., *Cancer Res.* 59:3346-51, 1999). Most β-catenin mutations are restricted at some codons in exon 3, and substitution mutations causing amino acid changes predominate in the β-catenin gene (Devereux, T. R. et al., *Mol. Carcinog.* 31:68-73, 2001; Udatsu, Y. et al., *Pediatr Surg. Int.* 17:508-512, 2001; Koch, A. et al., *Cancer Res.* 59:269-273, 1999; de La Coste, A. et al., *Proc. Natl. Acad. Sci. USA* 95:8847-8851, 1998).

Although it seems easy to detect β-catenin gene mutations using conventional methods, such as PCR-SSCP (single strand conformation polymorphism) and direct sequencing, technical problems associated with the low sensitivity of such β-catenin mutation detection methods have been reported (Abraham, S. C. et al., *Am. J. Pathol.* 158:1005-1010, 2001). Thus, there has been a need to develop a more reliable and faster mutation detection technique for β-catenin gene which can be used for various cancer studies, e.g., elucidation of the Wnt signaling related mechanism.

Studies have suggested that the high frequency MSI (microsatellite instability-H, MSI-H) colorectal cancer is not linked to *APC* mutations (Mirabelli-Primdahl, L. et al., *Cancer Res.* 59:3346-51, 1999), and that β-catenin gene mutations are mainly induced in MSI-H colorectal carcinomas (Mirabelli-Primdahl, L. et al., *Cancer Res.* 59:3346-51, 1999; Shitoh, K. et al., *Genes Chromosomes Cancer* 30:32-37, 2001).

Traverso et al. used MSI in the stool as a marker for the diagnosis of proximal colon cancers in stools (Traverso, G. et al., *Lancet.* 359:403-404, 2002), and several other markers, such as *APC, p53*, long DNA and K-ras, have been also used for colorectal cancer diagnosis using fecal DNA (Ahlquist, D. A. et al., *Gastroenterology* 119:1219-1227, 2000; Dong S. M. et al., *J. Natl. Cancer Inst.* 93:858-865, 2001).

The fact that β-catenin mutations are prone to occur in proximal colon cancers suggests β-catenin mutations might be used to diagnose proximal colon cancer. Accordingly, the present inventors have developed a β-catenin oligonucleotide microchip manufactured by fixing oligonucleotides on the surface of a solid matrix using an automatic microarrayer, the oligonucleotides being designed to detect various mutations at mutational hot spot regions of β-catenin gene. The β-catenin oligonucleotide microchip of the present invention can be used in studies to detect β-catenin mutations and to unravel the signal transduction mechanism and tumorigenesis related to β-catenin gene.

SUMMARY OF THE INVENTION

Accordingly, an object of the present invention is to provide a β-catenin oligonucleotide microchip which can be used as a fast and reliable genetic diagnostic device for studying the signal transduction mechanism and tumorigenesis related to β-catenin gene.

In accordance with one aspect of the present invention, there is provided a β-catenin oligonucleotide microchip for detecting β-catenin mutations comprising a plurality of oligonucleotides fixed on the surface of a solid matrix, wherein the oligonucleotides are designed to detect mutations in the mutational hot spots of β-catenin gene and a manufacturing process thereof.

In accordance with still another aspect of the present invention, there is provided a method for detecting β-catenin mutations employing same.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1:
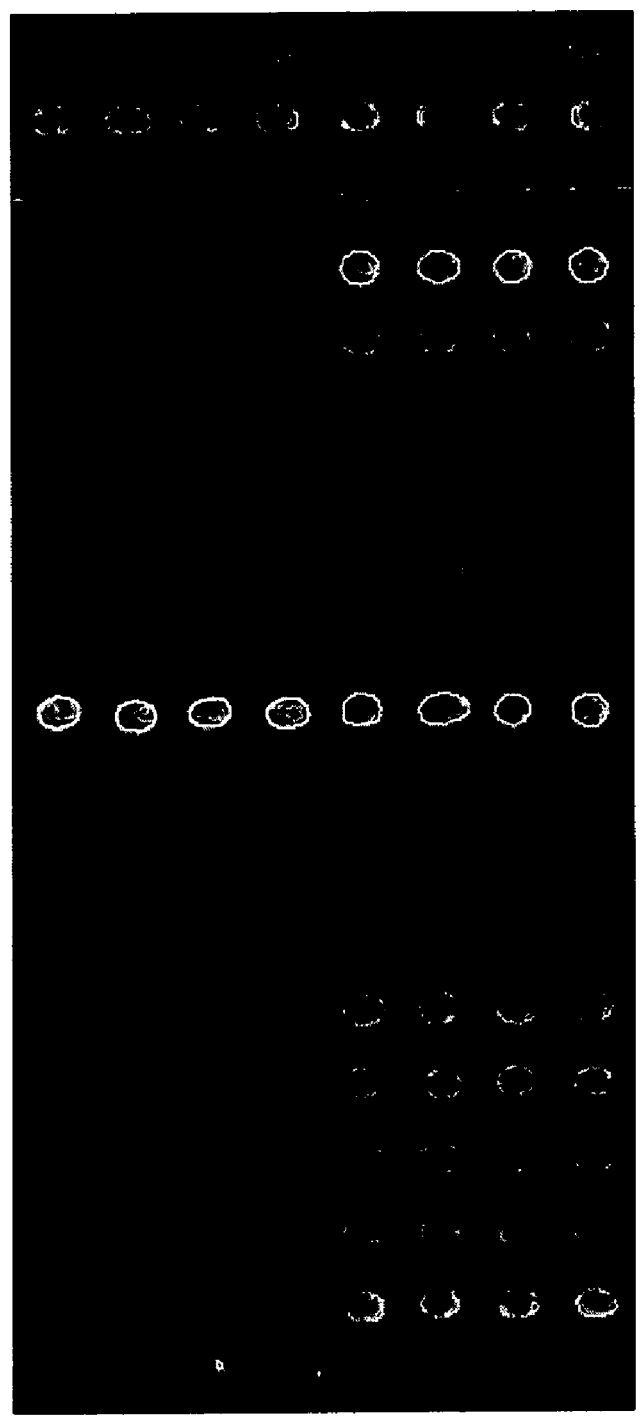
FIG. 1: the result of detecting ,β-catenin mutation in colon cancer tissue using the inventive β-catenin oligonucleotide microchip.

The present invention provides a β-catenin oligonucleotide microchip (hereinafter, referred to as "β-catenin oligo chip") for detecting β-catenin mutations, which comprises oligonucleotides fixed on the surface of a solid matrix using an automatic microarrayer, wherein the oligonucleotides are capable of detecting various mutations at mutational hot spot regions of β-catenin gene.

First, the oligonucleotides are designed to detect all possible missense mutations and in-frame deletions at 11 codons (codons 29, 31, 32, 33, 34, 35, 37, 38, 41, 45 and 48) in exon 3, mutational hot spots of β-catenin gene.

β-Catenin mutations have been identified in a variety of human malignancies, most of being missense mutations resctricted at hot-spot areas in exon 3. β-Catenin mutations are known to be associated with colorectal cancers with MSI. More than 70% of β-catenin mutations have been reported in colorectal cancers, and about 90% of those at the 11 codons in the hot spot region (codons 29, 31, 32, 33, 34, 35, 37, 38, 41, 45 and 48).

The present invention provides oligonucleotides which can be used to detect all possible mutations at the above mentioned hot spots of β-catenin gene, which occur at a frequency of more than 90% of all cases examined. Therefore, the β-catenin oligo chip of the present invention makes it possible to detect mutation at a confidence level of over 90%. In addition, since the oligonucleotides used in the inventive β-catenin oligo chip are designed to detect all possible missense mutations at the 11 codons, it is capable of detecting any missense mutation at these codons which have not yet been discovered. Further, the inventive β-catenin oligo chip also includes the oligonucleotides for detecting in-frame deletion (3-bp deletion) at each of the hot spot codons. Namely, as the inventive oligonucleotides are specifically designed to detect mutations at the hot spots of β-catenin gene taking the gene characteristics into consideration, the inventive β-catenin oligo chip provides improved accuracy and efficiency in detecting β-catenin gene mutation.

According to one aspect of the present invention, the inventive β-catenin oligo chip has 121 types of oligonucleotides spotted and fixed on the surface of a solid matrix, the oligonucleotides being capable of detecting various missense mutations and in-frame deletions at the 11 hot spot codons of β-catenin gene. Each oligonucleotide is spotted 4 times horizontally for increased accuracy of measured signals. Nine oligonucleotides (M) are designed to cover all possible substitutions at each hot spot codon, and one oligonucleotide (W) for the wild type. Thus, a total of 10 oligonucleotides are designed to detect missense mutations for codons 23, 29, 31, 32, 33, 34, 35, 38, 41 and 48. Further, 11 oligonucleotides (D) are designed to detect in-frame deletions (3-bp deletion) for each hot spot codon. In total, the 121 oligonucleotides cover all substitutions and in-frame deletions in the above 11 codons of exon 3.

Specifically, used for codon 29 are 9 types of substituted oligonucleotides obtained by replacing TCT (serine) with ACT (threonine), GCT (alanine), CCT (proline), TAT (tyrosine), TGT (cytosine), TTT (phenylalanine), TCA (serine), TCG (serine) and TCC (serine), respectively, and one deletion oligonucleotide obtained by deleting 3 bp of TCT. Used for codon 31 are 9 types of substituted oligonucleotides obtained by replacing CTG (leucine) with ATG (methionine), TTG (leucine), GTG (valine), CAG (glutamine), CGG (arginine), CCG (proline), CTA (leucine), CTC (leucine) and CTT (leucine), respectively; and one deletion oligonucleotide obtained by deleting 3 bp of CTG. Used for codon 32 are 9 types of substituted oligonucleotides obtained by replacing GAC (aspartic acid) with CAC (histidine), TAC (tyrosine), AAC (asparagines), GCC (alanine), GTC (valine), GGC (glycine), GAG (glutamic acid), GAT (aspartic acid) and GAA (glutamic acid), respectively; and one deletion oligonucleotide obtained by deleting 3 bp of GAC. Used for codon 33 are 9 types of substituted oligonucleotides obtained by replacing TCT (serine) with ACT (threonine), GCT (alanine), CCT (proline), TGT (cysteine), TAT (tyrosine), TTT (phenylalanine), TCA (serine), TCG (serine) and TCC (serine), respectively; and one deletion oligonucleotide obtained by deleting 3 bp of TCT. Used for codon 34 are 9 types of substituted oligonucleotides obtained by replacing GGA (glycine) with TGA (stop codon), AGA (arginine), CGA (arginine), GTA (valine), GCA (alanine), GAA (glutamic acid), GGT (glycine), GGG (glycine) and GGC (glycine), respectively; and one deletion oligonucleotide obtained by deleting 3 bp of GGA. Used for codon 35 are 9 types of substituted oligonucleotides obtained by replacing ATC (isoleucine) with GTC (valine), CTC (leucine), TTC (phenylalanine), ACC (threonine), AGC (serine), AAC (asparagine), ATG (methionine), ATA (isoleucine) and ATT (isoleucine), respectively; and one deletion oligonucleotide obtained by deleting 3 bp of ATC. Used for codon 37 are 9 types of substituted oligonucleotides obtained by replacing TCT (serine) with ACT (threonine), CCT (proline), GCT (alanine), TAT (tyrosine), TGT (cysteine), TTT (phenylalanine), TCA (serine), TCG (serine) and TCC (serine), respectively; and one deletion oligonucleotide obtained by deleting 3 bp of ACT. Used for codon 38 are 9 types of oligonucleotides obtained by replacing GGT (glycine) with AGT (serine), CGT (arginine), TGT (cysteine), GAT (aspartic acid), GCT (alanine), GTT (valine), GGA (glycine), GGG (glycine) and GGC (glycine), respectively; and one deletion oligonucleotide obtained by deleting 3 bp of GGT. Used for codon 41 are 9 types of substituted oligonucleotides obtained by replacing ACC (threonine) with TCC (serine), GCC (alanine), CCC (proline), AGC (serine), ATC (isoleucine), AAC (asparagine), ACA (threonine), ACT (threonine) and ACG (theronine), respectively; and one deletion oligonucleotide obtained by deleting 3 bp of ACC. Used for codon 45 are 9 types of substituted oligonucleotides obtained by replacing TCT (serine) with ACT (threonine), GCT (alanine), CCT (proline), TGT (cysteine), TAT (tyrosine), TTT (phenylalanine), TCA (serine), TCG (serine) and TCC (serine), respectively; and one deletion oligonucleotide obtained by deleting 3 bp of ACT. Used for codon 48 are 9 types of substituted oligonucleotides obtained by replacing GGT (glycine) with AGT (serine), TGT (cysteine), CGT (arginine), GAT (aspartic acid), GCT (alanine), GTT (valine), GGA (glycine), GGC (glycine) and GGG (glycine), respectively; and one deletion oligonucleotide obtained by deleting 3 bp of GGT.

One wild type of oligonucleotide (W) is designed for each codon to be directly compared with mutation types and to cover both homozygous and heterozygous mutations. For example, 12 oligonucleotides are spotted for codon 29, one is to detect a normal base sequence and the rest, the mutated base sequences. As a whole, 110 mutant oligonucleotides are designed for the 99 missense mutation types and 11 in-frame deletion types at the 11 hot spot codons, and 11 oligonucleotides, for the wild types and positive controls.

The β-catenin oligo chip of the present invention may be manufactured by fixing as many as 121 oligonucleotides on the surface of a solid matrix using an automatic microarrayer by a process comprising the steps of:

1) mixing each of the oligonucleotides in a micro spotting solution and distributing to a well plate;

2) spotting the oligonucleotide on the surface of a solid matrix using a microarrayer;

3) fixing the oligonucleotides on the solid matrix surface and washing;

4) denaturing the fixed oligonucleotides by soaking the solid matrix in 95° C. water, and then, treating the solid matrix with a sodium borohydride solution; and 5) washing and drying the solid matrix.

Each of the oligonucleotides used in step (1) preferably has a functional group that can be used to form a stable bond with the solid matrix surface. For example, each oligonucleotide may be linked with a 12 carbon spacer having a 5' amino modification, e.g., $H_2N-(CH_2)_{12}$-oligonucleotide. This amine group undergoes Schiff's base reaction with an aldehyde group on the solid matrix to form a firm bond therebetween. The 12 carbon spacer serves to enhance the hybridization rate by facilitating the contact between the oligonucleotide and a fluorescent dye-labeled target DNA.

The micro spotting solution used in step (1) may contain suitable salts and polymers to facilitate the application of the oligonucleotides on the solid matrix.

The solid matrix used in step (2) may be made of glass; modified silicone; plastic cassette; or polymer such as polycarbonate or a gel thereof. The surface of a solid matrix may be coated with a chemical compound that can serve to bind the oligonucleotide to the matrix substrate. Preferable chemicals that can be used for such coating have functional groups such as aldehyde or amine groups. In one preferred embodiment, the present invention uses a slide glass coated with an aldehyde.

According to one embodiment of steps (1) and (2), a total of 484 oligonucleotides are arranged in a specified manner on a solid matrix using an automatic pin microarrayer. Each oligonucleotide spot is preferably of circular shape with a diameter ranging from 100 to 500 µm. A preferable example of the solid matrix is a 3.7 cm×7.6 cm slide glass, which can accommodate approximately 100 to 10,000 spots per chip. Preferably, a total of 484 oligonucleotide spots, each of 130 µm diameter, may be arranged in multiple columns and rows at intervals of 200 to 800 µm.

In step (3), the oligonucleotides are fixed on the solid matrix surface by way of forming covalent bonds between the amine groups of the oligonucleotide and the aldehyde groups of the solid matrix via Schiff's base reaction. Free unreacted oligonucleotides are removed by washing the solid matrix with SDS, SSC, SSPE, etc.

In step (4), the fixed oligonucleotides are denatured, and unreacted aldehyde groups remaining on the solid matrix are reduced and inactivated by sodium borohydride treatment.

The β-catenin oligo chip of the present invention manufactured by the above process may be advantageously used to detect gene mutation, and this inventive method is much simpler and more economical than any of the conventional gene mutation detection methods: It takes several days to months on the average when the presence of gene mutation is examined using such conventional methods as SSCP (single strand conformation polymorphism), PTT (protein truncation test), RFLP (restriction fragment length polymorphism), cloning, direct sequencing, etc. However, analysis of a DNA sample for β-catenin gene mutation takes less than 10 to 11 hours when the inventive β-catenin oligo chip is employed. In addition, the β-catenin oligo chip of the present invention can be manufactured much more simply at a much less production cost than conventional chips. Once the required oligonucleotides are synthesized, it is possible to mass-produce the inventive slides. The amounts of reagents required when the inventive β-catenin oligo chip is used are far less than those required in any of the conventional methods.

The β-catenin oligo chip of the present invention is easy to manufacture using a pin microarrayer, while the existing Affymetrix oligo chip must be prepared using a complicated and expense photolithography technique.

Further, it is possible with the β-catenin oligo chip of the present invention to purify and modify the oligonucleotides, in contrast to the case of Affymetrix oligo chip which is prepared by directly synthesizing oligonucleotides on the surface of a solid matrix, wherein it is not possible to purify or modify the oligonucleotides. Accordingly, the inventive β-catenin oligo chip is capable of providing greater experimental accuracy than was possible before.

The present invention provides a method for detecting the β-catenin mutation employing the β-catenin oligo chip, which comprises the steps of:

1) preparing a fluorescent dye-labeled DNA sample from the blood of a subject patient;
2) reacting the labeled DNA sample with oligonucleotide spots on the β-catenin oligo chip;
3) washing the reacted oligo chip to remove unbound sample DNA;
4) detecting the mode of hybridization of specific oligonucleotide spots using a fluorescence reader; and
5) examining the presence of gene mutation.

In step (1), a DNA sample is prepared by incorporating a fluorescent dye into a blood DNA sample obtained from a subject patient. In the hybridization of fluorescent dye-labeled DNA with certain oligonucleotide spot on the oligo chip, it can be analyzed with a fluorescence reader using an appropriate software. Preferable fluorescent dyes include, but are not limited to, Cy5, Cy3, Texas Red, Fluorescein and Lissamine.

In step (2), the florescent dye-labeled DNA sample prepared in step (1) is mixed with a hybridization solution and transferred to each of the oligonucleotide. The hybridization reaction is performed in a 45~60° C. incubator saturated with water vapor for 3~9 hours. Then, the oligo chip is washed to remove unbound sample DNA and dried (step 3), and the resulting fluorescence is analyzed with a fluorescence reader using an appropriate software (step 4). In step (5), setting a maximum value at 99% reliable range as a threshold value, any signal showing a fluorescence level higher than the threshold is regarded positive for the presence of mutation.

The β-catenin oligo chip of the present invention can be effectively used to diagnose such cancer as colorectal carcinomas, endometrial cancer, stomach cancer, ovary cancer, hepatoblastoma cancer, etc. Since β-catenin gene function as a downstream transcriptional activator in the Wnt signaling pathway, the inventive β-catenin oligo chip can be used as an effective diagnostic tool for the study of signal transduction mechanism and tumorigenesis related to β-catenin gene.

The present invention investigated 74 colorectal carcinomas and 31 colorectal cancer cell lines for the presence of β-catenin mutations (see FIG. 1). All 5 β-catenin mutations were identified in proximal colon cancers (N=34), but β-catenin mutations were absent in 40 distal colorectal cancers. Four out of the 5 β-catenin mutations were point mutations at codons 32, 41 and 45, and the remaining one was in-frame deletion (3 bp deletion) at codon 45. In 31 colorectal cancer cell lines, 4 β-catenin mutations were identified. Three of these 4 mutations occurred at codon 45, and the remaining one occurred at codon 41.

In total 9 mutations were identified in the 74 colorectal carcinomas and 31 colorectal cancer cell lines. Six of the 9 mutations were found at codon 45 and 2 were at codon 41. Of the 6 mutations at codon 45, 4 were the identical missense mutations (TCT→TTT, Ser→Phe; in samples 395, 400, SNU-1047 and LSI17T) and 2 were the same in-frame deletion in samples 396 and HCT116. Codons 41 and 45 are known as GSK-3β phosphorylation sites and mutations at these sites might cause nuclear β-catenin accumulation (Saegusa, M. and Okayasu, I. *J. Pathol*. 194:59-67, 2001).

The remaining β-catenin mutation occurred at codon 32 in colon tissue 207. It has been proposed that codon 32 is important for β-catenin ubiquitination and proteasome-dependent degradation (Tong, J. H. et al., *Cancer Lett*. 163: 125-130, 1999). Mutations at codon 32 might influence serine 33 accessibility by GSK-3β kinase, thus preventing its phosphorylation (Koch, A. et al., *Cancer Res.* 59:269-273, 1999). It has been reported that specific codon 45 mutation (Ser45Phe) was frequent in colorectal carcinomas, and that codon 41 mutations, which predominate in hepatoblastomas, are rare in colorectal carcinomas (Koch, A. et al., *Cancer Res.* 59:269-273, 1999).

In the present invention, three of the 5 β-catenin mutations from colorectal cancers and three of the 4 β-catenin mutations from cell lines were identified at codon 45, and two of the 6 mutations at codon 45 were in-frame deletions. The in-frame deletion at codon 45 was previously reported in a colorectal cancer cell line and in colorectal carcinomas, but not in other types of cancer (Ilyas, M. et al., *Proc. Natl. Acad. Sci. USA* 94:10330-10334, 1997; Muller, O. et al., *Genes Chromosomes Cancer* 22:37-41, 1998). The in-frame deletion at codon 45 may result in the loss of highly conserved serine residues in a region of the protein that serves as a target for the enzyme GSK-3β (Ilyas, M. et al., *Proc. Natl. Acad. Sci. USA* 94:10330-10334, 1997). These results indicate that codon 45 including the in-frame deletion, are common in colorectal carcinomas but are not common in other types of cancer.

Mutational analysis of the β-catenin gene was performed using the oligonucleotide microarray. As the result of mutational analysis using the inventive. β-catenin oligo chip, the 9 β-catenin mutation positive samples in a total of 60 samples were detected. The present inventors compared the 9 β-catenin mutations detected by the β-catenin oligo chip with several techniques, e.g., PCR-SSCP, DHPLC, direct sequencing, and cloning-sequencing (see Table 2). Automatic direct sequencing, which has been widely used for mutational analysis was not capable of clearly detecting 2 of the 9 β-catenin mutations (see FIG. 2), and PCR-SSCP also missed one β-catenin mutation. These results might have been caused by excessive wild-type DNA in cancer tissues or by the low sensitivity of these two methods.

In the MSI study using the BAT-26 marker, the present invention confirms that MSI is intimately associated with proximal colon cancer, which agrees with previous reports ($p<0.01$) (Mirabelli-Primdahl, L. et al., *Cancer Res.* 59:3346-51, 1999; Traverso, G. et al., *Lancet.* 359:403-404, 2002). MSI was shown in 10 of 34 proximal colon carcinomas (29%), but in only 2 of 40 distal colorectal carcinomas (5%). In terms of the correlation between MSI and β-catenin mutations, β-catenin mutations were detected in 5 of the 12 (42%) colorectal carcinomas with MSI, but none of the 62 (0%) MSS colorectal carcinomas were found to harbor β-catenin mutations. All 5 β-catenin mutations detected in colon carcinomas with MSI were found in proximal colon cancers. These results confirm that MSI is involved in β-catenin mutations and demonstrate that β-catenin mutations are directly associated with proximal colon cancer.

It has been previously suggested that β-catenin mutations account for approximately are half of colorectal cancers with intact *APC* (Sparks, A. B. et al., *Cancer Res.* 59998:1130-1134, 1998). In the present invention, only one colorectal cancer cell line (SNU-1047) of the 9 samples with β-catenin mutations had *APC* mutations in the MCR. Recently, several groups have tried to diagnose colorectal cancers by using molecular markers such as *APC*, p53, long DNA, K-ras, etc (Traverso, G. et al., *Lancet.* 359:403-404, 2002; Ahlquist, D. A. et al., *Gastroenterology* 119:1219-1227, 2000; Dong, S. M. et al., *J. Natl. Cancer Inst.* 93:858-865, 2001). Three of 5 markers including MSI have been used for colorectal cancer diagnosis using fecal DNA (Traverso, G. et al., *Lancet.* 359:403-404, 2002). In addition, MSI has been used for the diagnosis of proximal colon cancers, which is difficult to detect because, among colorectal cancers, they are located furthest from the anus. β-Catenin may be a diagnostic marker for proximal colon cancer if β-catenin mutations correlate with the tumor's location in the proximal colon. The results of the present invention show MSI in 29% and β-catenin mutations in 15% of proximal colon cancers, respectively. Although all samples with β-catenin mutations exhibited MSI, β-catenin, alone or with MSI, may be used for the diagnosis of proximal colon cancer. Practically, such a system should not only be highly automated but also be usable as a high throughout diagnostic tool, especially if the substrate used in fecal DNA.

The following Examples and Test Examples are given for the purpose of illustration only, and are not intended to limit the scope of the invention.

EXAMPLE 1

Manufacture of β-Catenin Oligo Chip

Nine oligonucleotides were designed to cover all possible substitutions at 11 mutational hot spot codons of β-catenin gene (codons 23, 29, 31, 32, 34, 35, 37, 38, 41, 45 and 48), and one oligonucleotide for the wild-type. Further, one oligonucleotide was designed to detect in-frame deletions (3-bp deletion) at each of those codons. A total of 121 oligonucleotides was designed to cover all substitutions and in-frame deletions at the above 11 codons of exon 3.

The oligonucleotides described in SEQ ID Nos. 1, 12, 23, 34, 45, 56, 67, 78, 89, 100 and 111 are wild types. Oligonucleotides having missense mutation at one of the hot spot codons are: the oligonucleotides described in SEQ ID Nos. 2 to 10, at codon 29; the oligonucleotides described in SEQ ID Nos. 13 to 21, at codon 31; the oligonucleotides described in SEQ ID Nos. 24 to 32, at codon 32; the oligonucleotides described in SEQ ID Nos. 35 to 43, at codon 33; the oligonucleotides described in SEQ ID Nos. 46 to 54, at codon 34; the oligonucleotides described in SEQ ID Nos. 57 to 65, at codon 35; the oligonucleotides described in SEQ ID Nos. 68 to 76, at codon 37; the oligonucleotides described in SEQ ID Nos. 79 to 87, at codon 38; the oligonucleotides described in SEQ ID Nos. 90 and 98, at codon 41; the oligonucleotides described in SEQ ID Nos. 101 and 109, at codon 45; and the oligonucleotides described in SEQ ID Nos. 112 and 120, at codon 48.

Further, oligonucleotides having in-frame deletion at one of the hot spot codons are: the oligonucleotide described in SEQ ID No. 11, at codon 29; the oligonucleotide described in SEQ ID No. 22, at codon 31; the oligonucleotide described in SEQ ID No. 33, at codon 32; the oligonucleotide described in SEQ ID No. 44, at codon 33; the oligonucleotide described in SEQ ID No.55, at codon 34; the oligonucleotide described in SEQ ID No. 66, at codon 35; the oligonucleotide described in SEQ ID No. 77, at codon 37; the oligonucleotide described in SEQ ID No. 88, at codon 38; the oligonucleotide described in SEQ ID No. 99, at codon 41; the oligonucleotide described in SEQ ID No. 110, at codon 45; and the oligonucleotide described in SEQ ID No. 121, at codon 48.

All 121 oligonucleotides, each having a 12-carbon spacer to 5'-terminal modified with an amine residue which can undergo Schiff's base reaction with aldehyde groups, were obtained from MWG-Biotech (Ebrsberg, Germany) and purified by HPLC.

TABLE 1a

| SEQ ID No. | Oligonucleotide | Exon | Codon | Sequence |
|---|---|---|---|---|
| 1 | 29W | 3 | 29 | 5'-CAGCAACAGTCTTACCTGGAC-3' |
| 2 | 29M1 | | | 5'-GCAGCAACAGACTTACCTGGA-3' |
| 3 | 29M2 | | | 5'-GCAGCAACAGGCTTACCTGGA-3' |
| 4 | 29M3 | | | 5'-GCAGCAACAGCCTTACCTGGA-3' |
| 5 | 29M4 | | | 5'-CAGCAACAGTATTACCTGGAC-3' |
| 6 | 29M5 | | | 5'-CAGCAACAGTGTTACCTGGAC-3' |
| 7 | 29M6 | | | 5'-CAGCAACAGTTTTACCTGGAC-3' |
| 8 | 29M7 | | | 5'-AGCAACAGTCATACCTGGACT-3' |
| 9 | 29M8 | | | 5'-AGCAACAGTCGTACCTGGACT-3' |
| 10 | 29M9 | | | 5'-AGCAACAGTCCTACCTGGACT-3' |
| 11 | 29D | | | 5'-GGCAGCAACAGTACCTGGACT-3' |
| 12 | 31W | | 31 | 5'-CAGTCTTACCTGGACTCTGGA-3' |
| 13 | 31M1 | | | 5'-ACAGTCTTACATGGACTCTGG-3' |
| 14 | 31M2 | | | 5'-ACAGTCTTACTTGGACTCTGG-3' |
| 15 | 31M3 | | | 5'-ACAGTCTTACGTGGACTCTGG-3' |
| 16 | 31M4 | | | 5'-CAGTCTTACCAGGACTCTGGA-3' |
| 17 | 31M5 | | | 5'-CAGTCTTACCGGGACTCTGGA-3' |
| 18 | 31M6 | | | 5'-CAGTCTTACCCGGACTCTGGA-3' |
| 19 | 31M7 | | | 5'-AGTCTTACCTAGACTCTGGAA-3' |
| 20 | 31M8 | | | 5'-AGTCTTACCTCGACTCTGGAA-3' |
| 21 | 31M9 | | | 5'-AGTCTTACCTTGACTCTGGAA-3' |
| 22 | 31D | | | 5'-AACAGTCTTACGACTCTGGAA-3' |

TABLE 1b

| SEQ ID No. | Oligonucleotide | Exon | Codon | Sequence |
|---|---|---|---|---|
| 23 | 32W | 3 | 32 | 5'-TCTTACCTGGACTCTGGAATC-3' |
| 24 | 32M1 | | | 5'-GTCTTACCTGCACTCTGGAAT-3' |
| 25 | 32M2 | | | 5'-GTCTTACCTGTACTCTGGAAT-3' |
| 26 | 32M3 | | | 5'-GTCTTACCTGAACTCTGGAAT-3' |
| 27 | 32M4 | | | 5'-TCTTACCTGGCCTCTGGAATC-3' |
| 28 | 32M5 | | | 5'-TCTTACCTGGTCTCTGGAATC-3' |
| 29 | 32M6 | | | 5'-TCTTACCTGGGCTCTGGAATC-3' |
| 30 | 32M7 | | | 5'-CTTACCTGGAGTCTGGAATCC-3' |
| 31 | 32M8 | | | 5'-CTTACCTGGATTCTGGAATCC-3' |
| 32 | 32M9 | | | 5'-CTTACCTGGAATCTGGAATCC-3' |
| 33 | 32D | | | 5'-AGTCTTACCTGTCTGGAATCC-3' |
| 34 | 33W | | 33 | 5'-TACCTGGACTCTGGAATCCAT-3' |
| 35 | 33M1 | | | 5'-TTACCTGGACACTGGAATCCA-3' |
| 36 | 33M2 | | | 5'-TTACCTGGACGCTGGAATCCA-3' |
| 37 | 33M3 | | | 5'-TTACCTGGACCCTGGAATCCA-3' |
| 38 | 33M4 | | | 5'-TACCTGGACTGTGGAATCCAT-3' |
| 39 | 33M5 | | | 5'-TACCTGGACTATGGAATCCAT-3' |
| 40 | 33M6 | | | 5'-TACCTGGACTTTGGAATCCAT-3' |
| 41 | 33M7 | | | 5'-ACCTGGACTCAGGAATCCATT-3' |
| 42 | 33M8 | | | 5'-ACCTGGACTCGGGAATCCATT-3' |
| 43 | 33M9 | | | 5'-ACCTGGACTCCGGAATCCATT-3' |
| 44 | 33D | | | 5'-TTACCTGGACGGAATCCATTC-3' |

TABLE 1c

| SEQ ID No. | Oligonucleotide | Exon | Codon | Sequence |
|---|---|---|---|---|
| 45 | 34W | 3 | 34 | 5'-CTGGACTCTGGAATCCATTCT-3' |
| 46 | 34M1 | | | 5'-CCTGGACTCTTGAATCCATTC-3' |
| 47 | 34M2 | | | 5'-CCTGGACTCTAGAATCCATTC-3' |
| 48 | 34M3 | | | 5'-CCTGGACTCTCGAATCCATTC-3' |
| 49 | 34M4 | | | 5'-CTGGACTCTGTAATCCATTCT-3' |
| 50 | 34M5 | | | 5'-CTGGACTCTGCAATCCATTCT-3' |
| 51 | 34M6 | | | 5'-CTGGACTCTGAAATCCATTCT-3' |
| 52 | 34M7 | | | 5'-TGGACTCTGGTATCCATTCTG-3' |
| 53 | 34M8 | | | 5'-TGGACTCTGGGATCCATTCTG-3' |
| 54 | 34M9 | | | 5'-TGGACTCTGGCATCCATTCTG-3' |
| 55 | 34D | | | 5'-CCTGGACTCTATCCATTCTGG-3' |
| 56 | 35W | | 35 | 5'-GACTCTGGAATCCATTCTGGT-3' |
| 57 | 35M1 | | | 5'-GGACTCTGGAGTCCATTCTGG-3' |
| 58 | 35M2 | | | 5'-GGACTCTGGACTCCATTCTGG-3' |
| 59 | 35M3 | | | 5'-GGACTCTGGATTCCATTCTGG-3' |
| 60 | 35M4 | | | 5'-GACTCTGGAACCCATTCTGGT-3' |
| 61 | 35M5 | | | 5'-GACTCTGGAAGCCATTCTGGT-3' |
| 62 | 35M6 | | | 5'-GACTCTGGAAACCATTCTGGT-3' |
| 63 | 35M7 | | | 5'-ACTCTGGAATGCATTCTGGTG-3' |
| 64 | 35M8 | | | 5'-ACTCTGGAATACATTCTGGTG-3' |
| 65 | 35M9 | | | 5'-ACTCTGGAATTCATTCTGGTG-3' |
| 66 | 35D | | | 5'-GGACTCTGGACATTCTGGTGC-3' |

TABLE 1d

| SEQ ID No. | Oligo-nucleotide | Exon | Codon | Sequence |
|---|---|---|---|---|
| 67 | 37W | 3 | 37 | 5'-GGAATCCATTCTGGTGCCACT-3' |
| 68 | 37M1 | | | 5'-TGGAATCCATACTGGTGCCAC-3' |
| 69 | 37M2 | | | 5'-TGGAATCCATCCTGGTGCCAC-3' |
| 70 | 37M3 | | | 5'-TGGAATCCATGCTGGTGCCAC-3' |
| 71 | 37M4 | | | 5'-GGAATCCATTATGGTGCCACT-3' |
| 72 | 37M5 | | | 5'-GGAATCCATTGTGGTGCCACT-3' |
| 73 | 37M6 | | | 5'-GGAATCCATTTTGGTGCCACT-3' |
| 74 | 37M7 | | | 5'-GAATCCATTCAGGTGCCACTA-3' |
| 75 | 37M8 | | | 5'-GAATCCATTCGGGTGCCACTA-3' |
| 76 | 37M9 | | | 5'-GAATCCATTCCGGTGCCACTA-3' |
| 77 | 37D | | | 5'-TGGAATCCATGGTGCCACTAC-3' |
| 78 | 38W | | 38 | 5'-ATCCATTCTGGTGCCACTACC-3' |
| 79 | 38M1 | | | 5'-AATCCATTCTAGTGCCACTAC-3' |
| 80 | 38M2 | | | 5'-AATCCATTCTCGTGCCACTAC-3' |
| 81 | 38M3 | | | 5'-AATCCATTCTTGTGCCACTAC-3' |
| 82 | 38M4 | | | 5'-ATCCATTCTGATGCCACTACC-3' |
| 83 | 38M5 | | | 5'-ATCCATTCTGCTGCCACTACC-3' |
| 84 | 38M6 | | | 5'-ATCCATTCTGTTGCCACTACC-3' |
| 85 | 38M7 | | | 5'-TCCATTCTGGAGCCACTACCA-3' |
| 86 | 38M8 | | | 5'-TCCATTCTGGGGCCACTACCA-3' |
| 87 | 38M9 | | | 5'-TCCATTCTGGCGCCACTACCA-3' |
| 88 | 38D | | | 5'-AATCCATTCTGCCACTACCAC-3' |

TABLE 1e

| SEQ ID No. | Oligo-nucleotide | Exon | Codon | Sequence |
|---|---|---|---|---|
| 89 | 41W | 3 | 41 | 5'-GGTGCCACTACCACAGCTCCT-3' |
| 90 | 41M1 | | | 5'-TGGTGCCACTTCCACAGCTCC-3' |
| 91 | 41M2 | | | 5'-TGGTGCCACTGCCACAGCTCC-3' |
| 92 | 41M3 | | | 5'-TGGTGCCACTCCCACAGCTCC-3' |
| 93 | 41M4 | | | 5'-GGTGCCACTAGCACAGCTCCT-3' |
| 94 | 41M5 | | | 5'-GGTGCCACTATCACAGCTCCT-3' |
| 95 | 41M6 | | | 5'-GGTGCCACTAACACAGCTCCT-3' |
| 96 | 41M7 | | | 5'-GTGCCACTACAACAGCTCCTT-3' |
| 97 | 41M8 | | | 5'-GTGCCACTACTACAGCTCCTT-3' |
| 98 | 41M9 | | | 5'-GTGCCACTACGACAGCTCCTT-3' |
| 99 | 41D | | | 5'-TGGTGCCACTACAGCTCCTTC-3' |

TABLE 1e-continued

| SEQ ID No. | Oligo-nucleotide | Exon | Codon | Sequence |
|---|---|---|---|---|
| 100 | 45W | | 45 | 5'-ACAGCTCCTTCTCTGAGTGGT-3' |
| 101 | 45M1 | | | 5'-CACAGCTCCTACTCTGAGTGG-3' |
| 102 | 45M2 | | | 5'-CACAGCTCCTGCTCTGAGTGG-3' |
| 103 | 45M3 | | | 5'-CACAGCTCCTCCTCTGAGTGG-3' |
| 104 | 45M4 | | | 5'-ACAGCTCCTTGTCTGAGTGGT-3' |
| 105 | 45M5 | | | 5'-ACAGCTCCTTATCTGAGTGGT-3' |
| 106 | 45M6 | | | 5'-ACAGCTCCTTTTCTGAGTGGT-3' |
| 107 | 45M7 | | | 5'-CAGCTCCTTCACTGAGTGGTA-3' |
| 108 | 45M8 | | | 5'-CAGCTCCTTCGCTGAGTGGTA-3' |
| 109 | 45M9 | | | 5'-CAGCTCCTTCCCTGAGTGGTA-3' |
| 110 | 45D | | | 5'-CCACAGCTCCTCTGAGTGGTA-3' |

TABLE 1f

| SEQ ID No. | Oligo-nucleotide | Exon | Codon | Sequence |
|---|---|---|---|---|
| 111 | 48W | 3 | 48 | 5'-TCTCTGAGTGGTAAAGGCAAT-3' |
| 112 | 48M1 | | | 5'-TTCTCTGAGTAGTAAAGGCAA-3' |
| 113 | 48M2 | | | 5'-TTCTCTGAGTTGTAAAGGCAA-3' |
| 114 | 48M3 | | | 5'-TTCTCTGAGTCGTAAAGGCAA-3' |
| 115 | 48M4 | | | 5'-TCTCTGAGTGATAAAGGCAAT-3' |
| 116 | 48M5 | | | 5'-TCTCTGAGTGCTAAAGGCAAT-3' |
| 117 | 48M6 | | | 5'-TCTCTGAGTGTTAAAGGCAAT-3' |
| 118 | 48M7 | | | 5'-CTCTGAGTGGAAAAGGCAATC-3' |
| 119 | 48M8 | | | 5'-CTCTGAGTGGCAAAGGCAATC-3' |
| 120 | 48M9 | | | 5'-CTCTGAGTGGGAAAGGCAATC-3' |
| 121 | 48D | | | 5'-TTCTCTGAGTAAAGGCAATCC-3' |

Each oligonucleotide was mixed with a micro spotting solution (TeleChem International Inc, Sunnyvale, Calif.) at a mix ratio of 1:1, and 40 µl of each oligonucleotide was transferred to a 96 well plate. Twenty pmol/µl of oligonucleotides were spotted for codons 37, 41 and 45, and 40 pmol/µl for the remaining eight codons. After the charged 96 well plate was placed in a pin microarrayer (Microsys 5100 Cartesian, Cartesian Technologies Inc, Irvine, (Calif.), each oligonucleotide was printed on an aldehyde-coated glass slide (26×76×1 mm, CEL Associates Inc, Houston, Tex.). Spots, each of 130 µm diameter in size, were arranged in multiple columns and rows at intervals of 300 µm. The glass slide spotted with the oligonucleotides was washed twice with 0.2% SDS, and then, once with distilled water. The glass slide was soaked in hot water (95° C.) to denature the oligonucleotides, and then, in sodium borohydride solution for 5 minutes to inactivate unreacted aldehyde groups. Then, the glass slide was washed twice with 0.2% SDS, and then, once with distilled water, centrifuged, and dried.

EXAMPLE 2

Examination of β-Catenin Mutation using β-Catenin Oligo Chip (Step 1) Preparation of DNA Sample Specimens of 74 colorectal carcinomas were collected from Seoul National University Hospital and 31 colorectal cancer cell lines were obtained from the Korean Cell Line Bank (KCLB). Of the 74 colorectal cancers, 34 were from the proximal colon (cecum to splenic flexure) and 40 were from the distal colorectum (splenic flexure to rectum). Of 31 colorectal cancer cell lines, 7 originated from the proximal colon and 6 from the distal colorectum. The origin of the remaining 18 colorectal cancer cell lines was unknown. The gastric cancer cell lines SNU-638 and SNU-719 were used as positive controls for β-catenin mutations (Woo, D. K. et al., *Int. J. Cancer* 95:108-113, 2001). SNU-638 has β-catenin mutation at codon 41 (ACC→GCC, Thr→Ala) and SNU-791 mutation at codon 34 (GGA→GTA, Gly→Val).

Genomic DNA was extracted from frozen specimens using TRI reagent (Molecular Research Center, Cincinnati, Ohio, USA) or the automatic magnetic bead-based system (KingFisher, ThermoLabsystems, Finland), following the manufacture's instructions. To generate a fluorescent dye-labeled DNA sample, PCR amplification was performed using the extracted DNA as a template and two pairs of primers described in SEQ ID Nos. 122 to 125 (MWG-Biotech, Ebersberg, Germany). As shown in table 2, PCR primers of SEQ ID Nos. 122 and 123 for exon 3 were used as described in Mirabelli-Primdahl, L. et al. (*Cancer Res.* 59:3346-51, 1999), and PCR primers of SEQ ID Nos. 124 and 125 for interstitial large deletion of β-catenin gene were used as described in Udatsu Y. et al. (*Pediatr. Surg. Int.* 17:508-512, 2001).

Each PCR reaction solution (25 μl) contained 100 ng of genomic DNA, 10 pmol of each primer, 40 μM of dCTP, 20 μM of fluorescent dye Cy5-dCTP (MEN) or Cy3-dCTP (Amersham-biotech Ltd., Buckinghamshire, UK). Reactions were initiated by denaturation for 5 min at 94° C. in a programmable thermal cycler (Perkin Elmer Cetus 9600; Roche Molecular Systems, Inc., NJ). PCR conditions consisted of 35 cycles of 30 sec at 94° C., 30 sec at 56° C., and 1 min at 72° C., with a final elongation of 7 min at 72° C. After the PCR amplification, Cy5- or Cy3-labeled PCR product was purified using a purification kit (Qiagen Inc, Valencia, Calif.) and digested with 0.25 U of DNase I (Takara, Shiga, Japan) at 25° C. for 10 min. Remaining enzyme was inactivated at 85° C. for 10 min, removed by repeating the above purification procedure, and the Cy5- or Cy3-labeled DNA sample was recovered.

(Step 2) Hybridization Reaction and Analysis

The Cy5- or Cy3-labeled DNA samples prepared in step (1) were mixed and resuspended in 5× hybridization solution (TeleChem International Inc, Sunnyvale, Calif.) to a volume of 2~4 μl. Two μl of the mixed DNA sample prepared in Example 1 was dropped on the glass slide and the glass slide was covered with a cover glass. The hybridization reaction was performed by incubating the glass slide in a saturated vapor tube at 56° C. for 3 hours. The hybridized glass slide was rinsed at room temperature in a buffer of 0.2% SDS+ 2×SSC for 15~30 min, and then, in distilled water for 5 min, followed by centrifuging and drying. The glass slide was scanned using a ScanArray Lite (Parkard Instrument Co, Meriden, Conn.) and analyzed using Imagine (Biodiscovery, version 4.2) and Quantitative Microarray analysis software (QuantArrray, version 2.0).

Eleven wild type signals were compared to each other and adjusted to be equal by signal normalization. The remaining 110 signals at each codon were also adjusted in the same way as the wild type signals. After signal normalization, all signals were re-analyzed as previously described (Kim, I. J. et al., *Clin Cancer Res.* 8:457-463, 2002). The mean (BA) and the standard deviation (BSD) of the background signals were calculated, and the cutoff level was established to be BA+2.58BSD. (BA+2.58BSD) indicated the upper limit of the 99% confidence interval, and signals over this value were identified as meaningful signals. All data analysis was carried out using a SigmaPlot (SPSS Inc., San Rafael, Calif.), and means and standard deviations were calculated using Microsoft Excel program. The results of mutational analyses of colorectal carcinomas and colorectal cancer cell lines are shown in Table 3.

TABLE 2

| SEQ ID No. | Primer | Amplified region | Amplified size | Sequence |
|---|---|---|---|---|
| 122 | Exon-3F | Exon 3 | 218 bp | 5'-GATTTGATGGAGTTGGACATGG-3' |
| 123 | Exon-3R | | | 5'-TGTTCTTGAGTGAAGGACTGAG-3' |
| 124 | Long-3F | Part of exon 2~ | 1115 bp | 5'-AAAATCCAGCGTGGACAATGG-3' |
| 125 | Long-3R | part of exon 3 | | 5'-TGTGGCAAGTTCTGCATCATC-3' |

TABLE 3

| Sample | | β-catenin mutation | | | | APC |
|---|---|---|---|---|---|---|
| Name | Type | Location | Codon | Mutation | MSI | mutation |
| 207 | Tumor | Ascending[c] | 32 | GAC→AAC | +[f] | −[g] |
| 395 | Tumor | Ascending | 45 | TCT→TTT | + | − |
| 396 | Tumor | Ascending | 45 | In-frame deletion | + | − |

TABLE 3-continued

| Sample | | | β-catenin mutation | | | APC |
|---|---|---|---|---|---|---|
| Name | Type | Location | Codon | Mutation | MSI | mutation |
| 400 | Tumor | Ascending | 45 | TCT→TTT | + | – |
| 435 | Tumor | Ascending | 41 | ACC→GCC | + | – |
| SNU-407[a] | Cell line | Transverse[d] | 41 | ACC→GCC | + | – |
| SNU-1047[a] | Cell line | Transverse | 45 | TCT→TTT | + | 4107delC |
| LS174T[b] | Cell line | Colon[e] | 45 | TCT→TTT | + | – |
| HCT116[b] | Cell line | Colon | 45 | In-frame deletion | + | – |

[a]Oh, J. H. et al., Int. J. Cancer 81: 902-910, 1999
[b]Ilyas, M. et al., Proc. Natl. Acad. Sci. USA 94: 10330-10334, 1997
[c]Ascending colon
[d]Transverse colon
[e]Detailed information on the origin of these cell lines could not be found. It was confirmed that these cell lines originated from human colon adenocarcinomas.
[f]MSI in BAT-26
[g]No APC mutation was found in MCR As shown in Table 3, mutations of the β-catenin gene were identified in 5 (tissue samples 207, 395, 396, 400 and 435) of 74 colorectal carcinomas (5/14, 7%). These five β-catenin mutations were identified in 34 proximal colon cancers (5/34, 15%) and none were found in 40 distal colorectal cancers (0/40, 0%). Of 34 proximal colon cancers, five β-catenin mutations were found in 25 right-sided colon cancers, and no mutation, in the 9 traverse colon cancers. These results suggest that β-catenin mutations are associated with the tumors in the proximal colon (p=0.017).

In 31 colorectal cancer cell lines, 4 β-catenin mutations were found in cell lines SNU-407, SNU-1047, LS174T and HCT116. Of these 4 β-catenin mutations, two (SNU-407 and SNU-J1047) were found in cell lines originating from the proximal colon (traverse colon). The origins of the other 2 cell lines (LS174T and HCT116) harboring β-catenin mutations were not determined.

A total of 9 mutations were found among 74 colorectal cancer tissues and 31 colorectal cancer cell lines. Eight mutations out of these 9 mutations were identified at GSK-3β phosphrylation sites. All point mutations were amino acid substitutions and occurred at codons 32, 41 and 45. Six mutations were concentrated at codon 45. Four of these 6 point mutations at codon 45 were the identical missense mutations (TCT→TTT, Ser→Phe; in samples 395, 400, SNU-1047 and LS174T) and the remaining 2 mutations, the same in-frame deletions as in samples 396 and HCT116. No interstitial large deletion of the β-catenin gene was detected.

In the case of tissue 400, an additional signal in combination with wild type signals was observed, which indicated a missense mutation at codon 45 (TCT→TTT, Ser→Phe) (FIG. 1). Eight of the 9 samples with β-catenin mutations showed both wild type signals at each codon and an aberrant signal, which indicated the presence of heterozygous mutation. Meanwhile, LS174T showed only an abnormal signal in the absence of a wild type signal at codon 45, which means that LS174T has homozygous β-catenin mutation.

All 9 samples with the β-catenin mutations were investigated for APC mutations in the MCR (codons 1263-1513). Only one cell line (SNU-1047) harbored APC truncation mutation at codon 1369 (4107delC). The cell line LS174T, which had been reported not to carry β-catenin mutation was found to harbor β-catenin mutation (codon 45, TCT→TTT, Ser→Phe) in the present invention (Ilyas, M. et al., Proc. Natl. Acad. Sci. USA 94:10330-10334, 1997).

EXAMPLE 3

Confirmation of β-Catenin Mutations Detected by β-Catenin Oligo Chip

In order to confirm β-catenin mutations detected by the inventive β-catenin oligo chip, the nine β-catenin mutation samples were subjected to PCR-SSCP, DHPLC, PTT, cloning sequencing and direct sequencing as follows.

PCR-SSCP and DHPLC analyses were performed as previously described (Kim, I. J. et al., Int. J. Cancer 86:529-532, 2000; Wagner, T. et al., Genomics 62:369-376, 1999). DHPLC analysis was done using WAVE (Transgenomic, Omaha, Nebr.) and running conditions were optimized using WAVEMAKER software. A protein truncation test (PTT) was performed for mutation detection of the mutation cluster region (MCR, codon 1263-1513) of the APC gene, as previously described (Won, Y. J. et al., J. Hum. Genet. 44:103-108, 1999). During the cloning, fresh PCR products were ligated into PCR-TOPO vectors, and subcloned using the TA cloning system (Invitrogen, Carlsbad, Calif.). Bi-directional sequencing was performed using a Taq dideoxy terminator cycle sequencing kit and an ABI 3100 DNA sequencer (Applied Biosystems, Forster City, Calif.).

TABLE 4

| Sample | SSCP | DHPLC | Direct sequencing | Cloning sequencing | β-catenin oligo chip |
|---|---|---|---|---|---|
| 207 | +[a] | + | ND | + | + |
| 395 | + | + | + | + | + |
| 396 | + | + | + | + | + |
| 400 | ND[b] | + | ND | + | + |
| 435 | + | + | + | + | + |
| SNU-407 | + | + | + | + | + |
| SNU-1047 | + | + | + | + | + |
| LS174T | + | + | + | + | + |
| HCT116 | + | + | + | + | + |

[a]Detected
[b]Not detected

Figure 2:
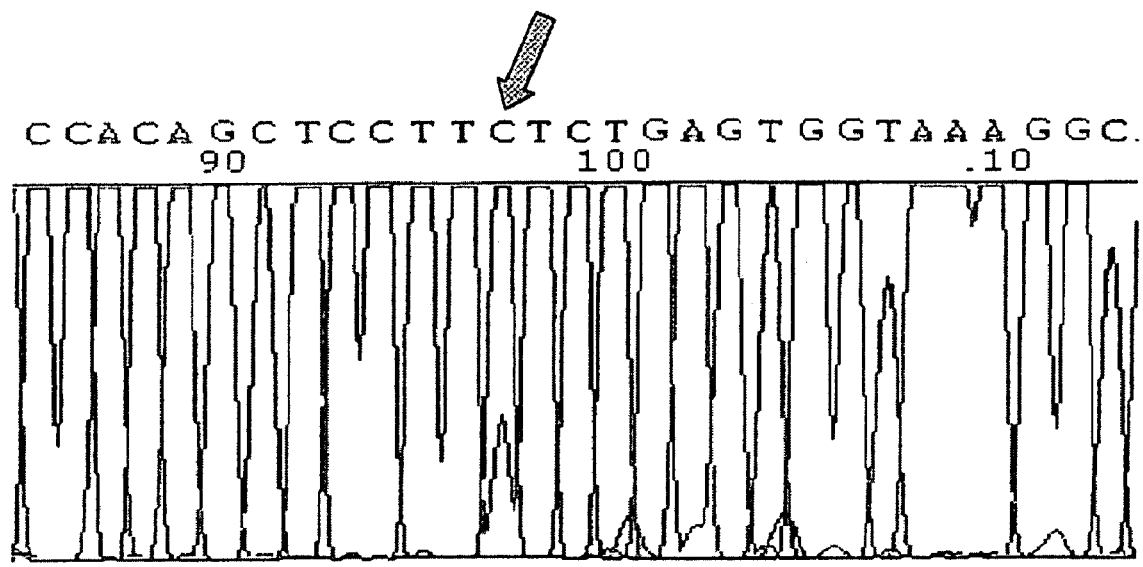
FIG. 2: the direct sequencing result of colon cancer tissue which has a β-catenin mutation confirmed by the inventive β-catenin oligonucleotide microchip.

Among the conventional techniques, the automatic direct sequencing method, which has been widely used for mutational analysis, did not clearly detect 2 of the 9 β-catenin mutations (FIG. 2). PCR-SSCP also missed one β-catenin mutation. These results might have been caused by excessive wild type DNA in cancer tissues or by the low sensitivity of these two methods.

EXAMPLE 4

Relationship between β-Catenin Mutations and MSI

It has been reported that MSI status can be meaningfully correlated with proximal colon cancers, and MSI may be used as a diagnostic marker for the diagnosis of proximal colon cancer (Traverso, G. et al., *Lancet*. 359:403-403, 2002). To determine the MSI status, genomic DNAs extracted from 74 colorectal carcinomas were subjected to PCR using BAT-26 marker (Shitoh, K. et al., *Genes Chromosomes Cancer* 30:32-37, 2001; Samowits, W. S. et al., *Am. J. Pathol.* 158:1517-1524, 2001).

Each PCR reaction solution (25 μl) contained 100 ng of genomic DNA extracted from normal and cancer tissues using Picoll-Paque and Trizol reagents, 10 pmol of each BAT26-F and BAT26-R primers of SEQ ID Nos. 126 and 127 0.25 μl, 2.5 mM of dNTP 0.5 μl, 10× PCR buffer solution 2.5 μl, [α-$^{32}$P]dCTP 0.25 μl, and Taq DNA polymerase (5 unit/μl). Reactions were initiated by denaturation for 5 min at 94° C. in a programmable thermal cycler (Perkin Elmer Cetus 9600; Roche Molecular Systems, Inc., N.J.). PCR conditions consisted of 35 cycles of 30 sec at 94° C., 30 sec at 52° C., and 1 min at 72° C., with a final elongation of 7 min at 72° C. The reaction mixture was heated at 95° C. for 5 min and cooled down in a ice bath. Thirty-five μl of the cooled reaction mixture was subjected to 40% polyacrylamide gel (29:1) electrophoresis, and the gel was dried and exposed to X-ray.

To determine the correlations between the β-catenin mutations, MSI and tumor location, statistical analyses were performed using the $\chi^2$ or Fisher's exact test, setting a=0.05 as the significance level using the STATISTICA software (StatSoft Inc., Tulsa, Okla.).

As a result, 12 of 74 colorectal cancer tissues (16%) showed MSI in the BAT-26 marker. 10 out of 34 proximal colon cancers (29%) were found to carry MSI and only 2 of 40 distal colorectal cancers (5%) were found to harbor MSI. MSI was statistically correlated with the proximal location ($p<0.01$). All 5 β-catenin mutations were found in 12 colorectal cancers with MSI (5/12, 42%) and none were found in 62 colorectal cancers with MSS (microsatellite stability). β-catenin mutations were more common in colorectal carcinomas with MSI than in those with MSS ($p<0.001$).

While the embodiments of the subject invention have been described and illustrated, it is obvious that various changes and modifications can be made therein without departing from the spirit of the present invention which should be limited only by the scope of the appended claims.

What is claimed is:

1. A β-catenin oligonucleotide microchip for detecting β-catenin mutations at each of 11 hot spot codons inclusive of codons 29, 31, 32, 33, 34, 35, 37, 38, 41, 45 and 48, respectively, comprising a plurality of oligonucleotides fixed on the surface of a solid matrix, wherein the oligonucleotides are those of SEQ ID Nos: 1 to 121.

* * * * *